United States Patent
Von Hollen

(10) Patent No.: US 10,864,542 B2
(45) Date of Patent: Dec. 15, 2020

(54) ASSEMBLY FOR USE IN A LIQUID DROPLET APPARATUS

(71) Applicant: KONINKLIJKE PHILIPS N.V., Eindhoven (NL)

(72) Inventor: Dirk Ernest Von Hollen, Clark, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 224 days.

(21) Appl. No.: 15/105,600

(22) PCT Filed: Dec. 11, 2014

(86) PCT No.: PCT/EP2014/077300
§ 371 (c)(1),
(2) Date: Jun. 17, 2016

(87) PCT Pub. No.: WO2015/091171
PCT Pub. Date: Jun. 25, 2015

(65) Prior Publication Data
US 2016/0310982 A1    Oct. 27, 2016

(30) Foreign Application Priority Data
Dec. 19, 2013  (EP) ..................... 13198614

(51) Int. Cl.
*B05B 17/06*   (2006.01)
*B05B 17/00*   (2006.01)
*A61M 11/00*   (2006.01)
*A61M 16/00*   (2006.01)

(52) U.S. Cl.
CPC ....... *B05B 17/0653* (2013.01); *A61M 11/005* (2013.01); *A61M 16/0054* (2013.01); *B05B 17/0646* (2013.01)

(58) Field of Classification Search
CPC . B05B 17/0653; B05B 17/0646; B05B 17/06; B05B 1/02; B05B 1/083; B05B 1/185; A61M 11/005; A61M 16/0054
USPC ....................................... 239/102.2
See application file for complete search history.

(56) References Cited

U.S. PATENT DOCUMENTS

| | | | |
|---|---|---|---|
| 3,790,079 A | 2/1974 | Berglund | |
| 4,605,167 A | 8/1986 | Maehara | |
| 6,629,646 B1 * | 10/2003 | Ivri | ...................... A61M 11/005 239/102.2 |
| 6,732,944 B2 * | 5/2004 | Litherland | ........... A61M 11/005 239/102.1 |

(Continued)

FOREIGN PATENT DOCUMENTS

| | | |
|---|---|---|
| CN | 103201047 A | 7/2012 |
| DE | 202012105005 U1 | 1/2013 |

(Continued)

*Primary Examiner* — Tuongminh N Pham
(74) *Attorney, Agent, or Firm* — Daniel H. Brean

(57) ABSTRACT

An assembly for use in a liquid droplet apparatus comprises a vibrating element (201), an aperture plate (205) and a vibrating platform (203). The vibrating platform is positioned between the vibrating element and the aperture plate for conveying vibrations from the vibrating element to the aperture plate. The vibrating platform (203) is structured such that the aperture plate (205) is located within a cavity (202) formed in the vibrating platform.

13 Claims, 2 Drawing Sheets

(56) References Cited

U.S. PATENT DOCUMENTS

| | | | |
|---|---|---|---|
| 6,948,491 B2 * | 9/2005 | Loeffler | A61M 15/0028 |
| | | | 128/200.14 |
| 7,607,589 B2 * | 10/2009 | Yu | B05B 17/0646 |
| | | | 239/102.2 |
| 7,931,212 B2 * | 4/2011 | Urich | A61M 11/005 |
| | | | 239/102.1 |
| 9,108,211 B2 * | 8/2015 | Ivri | B05B 17/0646 |
| 9,126,218 B2 | 9/2015 | Sasaki | |
| 9,333,522 B2 | 5/2016 | Hsieh | |
| 9,533,323 B2 | 1/2017 | Sauzade | |
| 2002/0162898 A1 | 11/2002 | Klimowicz | |
| 2004/0050947 A1 * | 3/2004 | Power | A61M 11/005 |
| | | | 239/4 |
| 2006/0243820 A1 | 11/2006 | Ng | |
| 2007/0051827 A1 * | 3/2007 | Shen | B05B 17/0646 |
| | | | 239/102.2 |
| 2009/0134235 A1 | 5/2009 | Ivri | |
| 2009/0242660 A1 | 10/2009 | Yu | |
| 2010/0031968 A1 | 2/2010 | Sheikh et al. | |
| 2010/0319685 A1 | 12/2010 | Yu | |
| 2012/0060833 A1 | 3/2012 | Achtzehner | |
| 2013/0270358 A1 | 10/2013 | Hsieh | |

FOREIGN PATENT DOCUMENTS

| | | |
|---|---|---|
| JP | 2013141532 A | 7/2013 |
| RU | 2349392 | 3/2009 |
| WO | WO2012092163 A1 | 7/2012 |
| WO | WO2012156724 A2 | 11/2012 |
| WO | WO2014005711 A1 | 1/2014 |
| WO | WO2014097939 A1 | 6/2014 |

\* cited by examiner

ASSEMBLY FOR USE IN A LIQUID DROPLET APPARATUS

CROSS-REFERENCE TO RELATED APPLICATIONS

This patent application claims the priority benefit under 35 U.S.C. § 371 of international patent application no. PCT/EP2014/077300, filed Dec. 11, 2014, which claims the benefit of European Patent Application No. EP13198614.3, filed on Dec. 19, 2013, which is hereby incorporated by reference herein.

TECHNICAL FIELD

The invention relates to an assembly for use in a liquid droplet apparatus for producing liquid droplets, for example for use in ultrasonic mesh aerosol nebulizer devices, and in particular to an assembly such as a mesh sub-assembly.

BACKGROUND

Aerosol generators are used in various industries to produce fine droplets. For example, nebulisers deliver pharmaceuticals in droplet form, for example for inhalation.

There are many known nebuliser designs, which include human and spring powered devices. Much recent research has been directed to the use of electrically powered nebulizers, for example jet nebulisers (also called atomizers), which force a gas through a liquid containing the medicine, ultrasonic wave nebulisers, in which a piezoelectric element vibrates a column of liquid to produce a vapour mist, and vibrating mesh technology, in which an aperture plate is vibrated against the surface of a liquid reservoir, or has a supply of liquid supplied directly to the aperture plate. The aperture plate may comprise a mesh, a screen, a membrane, a machined metal plate, a polymer or the like, having many tiny openings or micro nozzles. When the aperture plate is vibrated (usually by a piezoelectric element), fine droplets are dispensed.

Nebulizers of this type comprise a mesh sub-assembly, often in the form of a ring, in which an aperture plate (such as a screen, mesh, membrane, machine metal plate, polymer or the like, as mentioned above) is coupled to a vibrating source (such as a piezoelectric element).

Previous ring style mesh aerosol systems are described with a surface island and a three dimensional structure that protrudes from a mounting plate, or as a single piece structure in which the mesh is permanently attached to the vibrating structure. Ring style mesh aerosol arrangements of this type are formed with the mesh being attached to the external surface or top of the island.

FIG. 1 shows a mesh sub-assembly in which a aperture plate 105 is coupled to a vibrating platform 103, using as a non-limitative example an adhesive 107. The vibrating platform 103 couples the aperture plate 105 with a vibrating element 101 (such as a piezoelectric ring element). The vibrating platform 103 acts to transmit vibrations received from the vibrating element 101 to the aperture plate 105. The arrow shows the direction of spray during use, based on liquid being applied to the aperture plate 105 is a corresponding direction. During use, contraction of the vibrating element 101 in an inward radial direction causes the angled structure to become less angled or less sloped, i.e. more orthogonal to a plane in which the vibrating element 101 lies, thus causing the aperture plate 105 to move in a forward direction, that is towards the bottom of the page in the Figure, or in the direction of spray as shown by the arrow in FIG. 1.

As can be seen from FIG. 1, in such an arrangement the aperture plate 105 protrudes from the assembly. This has a disadvantage of requiring additional space. Furthermore, the aperture plate 105 is susceptible to being inadvertently dislodged or removed.

SUMMARY

It is an aim of the present invention to provide an apparatus or method which obviates or reduces at least one or more of the disadvantages mentioned above.

According to a first aspect of the present invention there is provided an assembly for use in a liquid droplet apparatus. The assembly comprises a vibrating element, an aperture plate and a vibrating platform. The vibrating platform is positioned between the vibrating element and the aperture plate, for conveying vibrations from the vibrating element to the aperture plate. The vibrating platform is structured such that the aperture plate is located within a cavity formed in the vibrating platform.

This has the advantage of protecting the aperture plate from accidental dislodgement from the vibrating platform. This structure also has the advantage of reducing the overall height of the assembly.

BRIEF DESCRIPTION OF THE DRAWINGS

For a better understanding of examples of the present invention, and to show more clearly how the examples may be carried into effect, reference will now be made, by way of example only, to the following drawings in which.

DETAILED DESCRIPTION

Preliminary, it should be clearly understood that in the meaning of the invention the terms "vibrating element" and "vibrating platform" equally designate or be construed as an element and a platform that are configured to vibrate, respectively. It should further be clear that in the meaning of the invention any vibration related to this element of platform should occur during use only.

Figure 2:
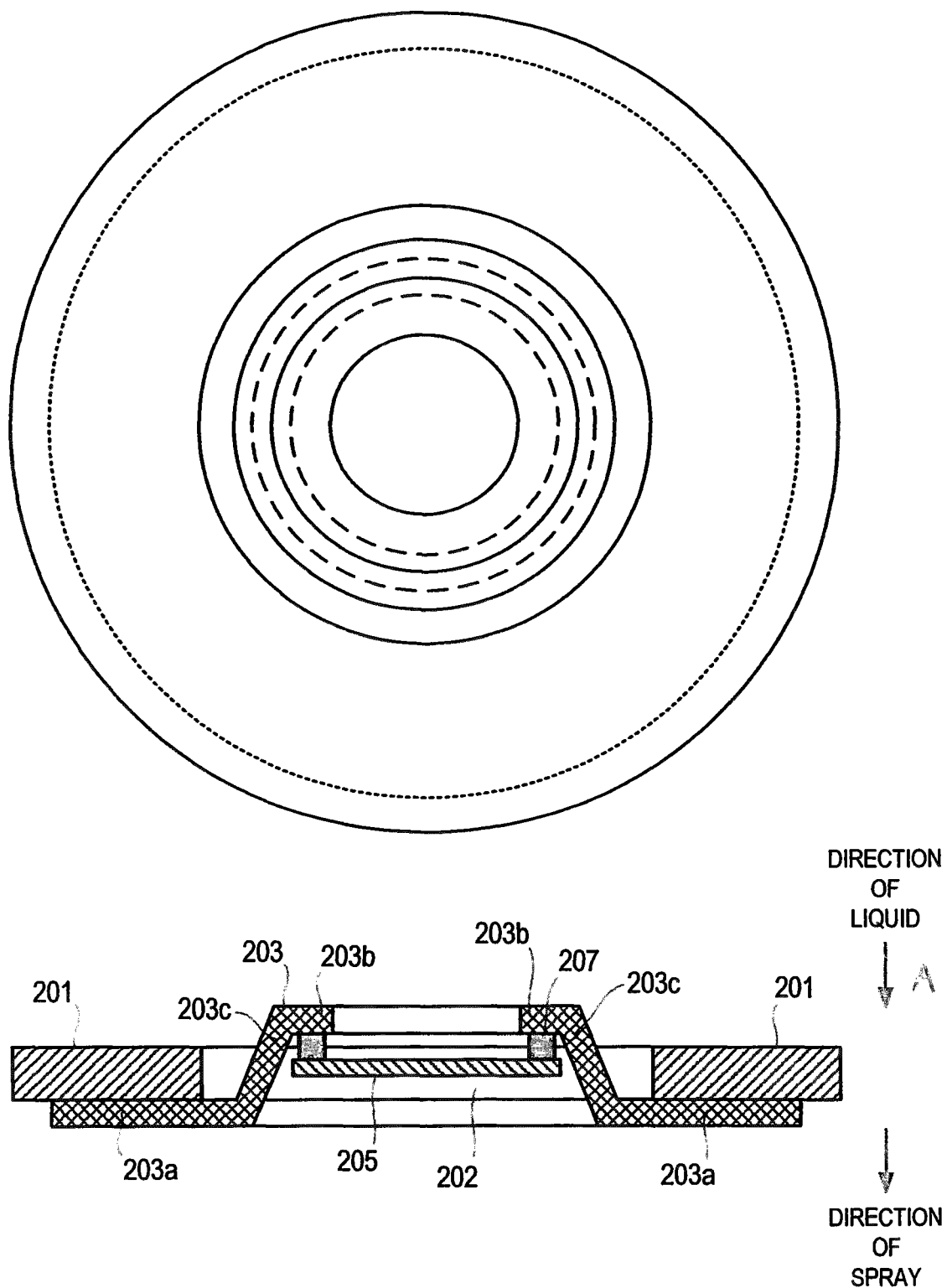
FIG. 2 shows an embodiment of the present invention.

FIG. 2 shows a cross-sectional view and a plan view of an assembly according to an embodiment of the present invention, for use in a liquid droplet apparatus.

The assembly comprises a vibrating element 201, an aperture plate 205 and a vibrating platform 203. The vibrating platform 203 is positioned between the vibrating element 201 and the aperture plate 205 for conveying vibrations from the vibrating element 201 to the aperture plate 205. The vibrating platform 203 is structured such that the aperture plate 205 is located within a cavity 202 formed in the vibrating platform 203.

In the example of FIG. 2 the vibrating element 201 takes the form of an annular vibrating element, for example an annular piezoelectric device, also known as a piezoelectric ring, wherein during use the annular piezoelectric device is radially expandable and contractable upon actuation thereof, i.e. vibrates in a radial direction. The annular piezoelectric device also vibrates in an axial direction.

The aperture plate 205 may comprise, for example, a mesh, a screen, a membrane, a machined metal plate (for example involving electroforming and laser ablation), a polymer or the like, having many tiny openings or micro nozzles. For example, the aperture plate 205 may be flat as shown, or domed in shape.

The embodiment of FIG. 2 has the advantage of protecting the aperture plate 205 from accidental dislodgement from the vibrating platform (by the manner in which it is located within a cavity 202 formed by the vibrating platform 203).

In the example of FIG. 2 the vibrating platform 203, having the aperture plate 205 arranged within a cavity 202 thereof, is structured such that a sidewall 203c of the vibrating platform (coupling a first annular portion 203a and a second annular portion 203b) protrudes at least partly through the opening in the annular vibrating element 201. This has the further advantage of reducing the overall height of the assembly.

Figure 1:
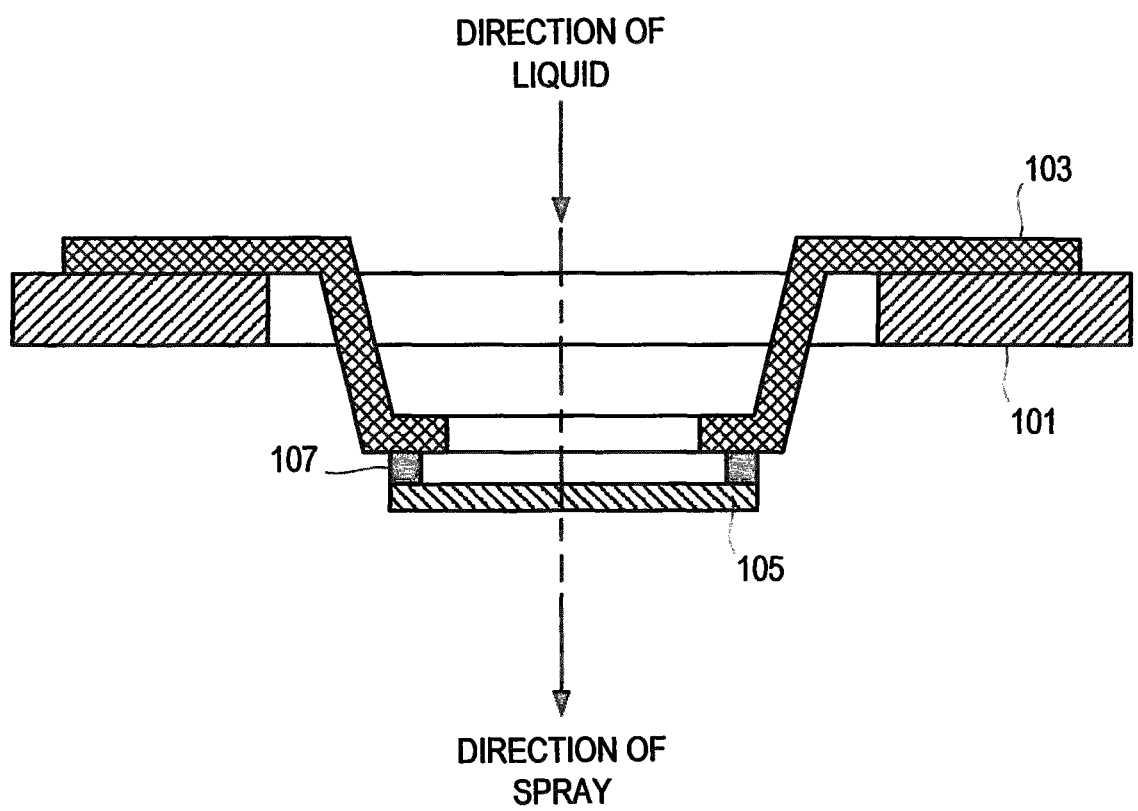
FIG. 1 shows a known sub-assembly.

The assembly of FIG. 2 is therefore effectively inverted compared to the structure of FIG. 1, with the vibrating platform 203 being attached, in this example, to the vibrating element 201 on a side corresponding to the direction of spray. In such an example, movement of the aperture plate in a direction of the spray (referred to herein as a "forward" direction) is caused by expansion of the vibrating element in an outwardly radial direction, rather than by contraction in an inwardly radial direction as required in FIG. 1.

It is noted that, if desired, the direction of spray can be reversed in FIG. 2 by changing the direction in which liquid is applied to the aperture plate, for example such that the direction of liquid and direction of spray are opposite to that shown in FIG. 2. In such an embodiment a "forward" movement of the aperture plate 205 is obtained by contraction of the vibrating element 201 in an inwardly radial direction, similar to that of FIG. 1.

In FIGS. 2 to 3, the first annular portion 203*a* of the vibrating platform can be fixedly coupled to an annular portion of the vibrating element 201, and the second annular portion 203*b* can be fixedly coupled to the aperture plate 205.

For example, the aperture plate 205 may be coupled to the vibrating platform 203 using adhesive 207, and the first portion 203*a* of the vibrating platform may be fixedly connected to the vibrating element 201 using an adhesive (not shown).

The embodiments of the present invention allow the aperture plate component 205 to vibrate in direction "A" when the annular piezoelectric element expands outward in a radial direction, in contrast to traditional mesh ring style aerosol generators which rely on the inward radial movement to provide a compression force to the mesh in order to vibrate in direction "A", which can also be termed a "forward" direction. The forward direction action allows fluid to be transmitted from the back side surface to the micro nozzles to the front surface as a spray. The embodiments of the present invention can therefore operate effectively in reverse compared to a conventional device, i.e. radial expansion rather than contraction of the annular piezoelectric device causes a forward movement of the aperture plate 205 in direction "A". This has the advantage of requiring less power to deliver a higher output rate of aerosol.

The inward cone or cavity defined by the embodiments of the invention provides a means of a built in barrier to prevent accidental removal of the aperture plate 205, for example protecting the aperture plate from being inadvertently removed from the adhesive which affixes the aperture plate to the vibrating platform 203.

The vibrating platform 203 may comprise at least one flexible joint (for example a joint which is non-stressed during manufacture), for allowing additional movement of the vibrating platform in response to movement of the vibrating element in a radial direction. This allows for additional movement (amplitude)", in a similar manner as a speaker when more power is added. Thus, having a flexible joint enables a greater amplitude of movement to be obtained for a given power that is applied to the piezoelectric device. This has the advantage of being able to increase the amplitude of movement without having to necessarily increase the power applied to the piezoelectric device, which can have power saving advantages, in addition to preventing damage to the piezoelectric device.

The geometry related to the inward facing structure that expands in the outward radial motion of a ring style piezo vibrator, provides the advantages of being able to move the aperture plate in response to radial movement of the vibrating element, and also protect the aperture plate within the cavity formed by the inward facing structure.

According to one embodiment the vibrating platform comprises a first surface for coupling to a vibrating element, and a second surface for coupling to an aperture plate, the plane of the first surface being separated from the plane of the second surface by sidewalls that couple the first and second surface.

The sidewalls define a cavity. The aperture plate is located within the cavity, on a side of the second surface which is inward facing to the cavity.

The embodiments of the invention can be applied to any form of respiratory drug delivery apparatus, including a nebulizer or atomizer. Applications include, for example, respiratory care or sleep assistance nebulizer for delivery for home humidification via nasal cannula or mask.

The embodiments of the invention can be used to support efforts in home health care solutions as a part of a liquid nebulizer drug delivery system, or a humidification system for critical or home ventilation or sleep or nasal cannula via oxygen.

The embodiments of the invention provide an improved ultrasonic mesh aerosol nebulizer, in which the mesh subassembly is equal or lower than a piezo ring assembly.

It is noted that, in any of the embodiments described above, the aperture plate can take other shapes or forms, for example in addition to the flat or domed shapes described herein.

According to one embodiment there is provided an assembly for use in a liquid droplet apparatus. The assembly comprises a vibrating element, an aperture plate and a vibrating platform for coupling the vibrating element and the aperture plate. The vibrating platform is structured such that the aperture plate is positioned within a conical structure formed by the vibrating platform.

According to another embodiment there is provided an assembly for use in a liquid droplet apparatus. The assembly comprises a vibrating element, an aperture plate and a vibrating platform for coupling the vibrating element and the aperture plate. The vibrating platform is formed from an inverted structure, such that the aperture plate is positioned within a conical structure formed by the vibrating platform.

The sidewalls of the vibrating platform may be angled with respect to a plane of the vibrating element, and wherein expansion of the vibrating element in an outwardly radial direction causes the sidewalls of the vibrating platform to become more orthogonal with respect to the plane of the vibrating element, thereby causing the aperture plate to move in a forward direction.

The vibrating platform may be circular in shape, and comprise a first surface for coupling to the vibrating element, and a second surface for coupling to the aperture plate, the plane of the first surface being separated from the plane of the second surface by a sidewall that couples the first and second surfaces.

The aperture plate may be located within the cavity, on a side of the second surface which is inward facing to the cavity.

The sidewall may be angled with respect to the plane of the vibrating element. In such an embodiment, the angle of the sidewall is adjusted through contraction and expansion of the vibrating element in a radial direction in the plane of the vibrating element.

The vibrating platform may comprise a joint which is non-stressed during manufacture, for allowing additional movement of the vibrating platform in response to movement of the vibrating element in a radial direction.

Although the examples show the diameter of the annular vibrating element 201 being larger than the diameter of the first annular portion 203a of the vibrating platform 203, it is noted that the diameter of the annular vibrating element 201 may be smaller than, or equal to, the diameter of the first annular portion 203a of the vibrating platform 203, without departing from the scope of the invention as defined in the appended claims.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single processor or other unit may fulfil the functions of several units recited in the claims. Any reference signs in the claims shall not be construed so as to limit their scope.

The invention claimed is:

1. An assembly for use in a liquid droplet apparatus, the assembly comprising:
    a vibrating element;
    an aperture plate; and
    a vibrating platform;
    wherein the vibrating platform is positioned between the vibrating element and the aperture plate for conveying vibrations from the vibrating element to the aperture plate, wherein the vibrating platform comprises a first annular portion for coupling to the vibrating element, a second annular portion for coupling to the aperture plate, and a sidewall to define a cavity;
    wherein the first annular portion lies in a first plane and the second annular portion lies in a second plane, the second plane being separated from and substantially in parallel with the first plane, and separated from and substantially in parallel with a third plane corresponding to a plane in which the vibrating element lies,
    wherein the sidewall protrudes at least partly through an aperture of the vibrating element,
    wherein the vibrating platform is structured such that the aperture plate is located within the cavity formed in the vibrating platform defined by the sidewall,
    wherein the sidewall is angled with respect to the plane of the vibrating element so that the angle of the sidewall is adjusted through contraction and expansion of the vibrating element in a radial direction in the plane of the vibrating element, and
    wherein the cavity has a conical shape when the vibrating element is not actuated.

2. The assembly as claimed in claim 1, wherein the vibrating element comprises an annular piezoelectric device, wherein during use the annular piezoelectric device is radially expandable and contractable upon actuation thereof.

3. The assembly as claimed in claim 1, wherein the sidewall of the vibrating platform is angled with the respect to the first and second planes of the vibrating platform, and is configured such that any expansion of the vibrating element during use in a radially outward direction causes the sidewall of the vibrating platform to become less orthogonal with respect to the first and second planes of the vibrating platform, thereby causing the aperture plate to move, during use, in a direction corresponding to a direction of spray.

4. The assembly as claimed in claim 1, wherein the first annular portion of the vibrating platform is fixedly coupled to an annular portion of the vibrating element, and the second annular portion of the vibrating platform is fixedly coupled to the aperture plate.

5. The assembly as claimed in claim 1, wherein the vibrating platform is configured such that the sidewall of the vibrating platform passes through the aperture in the vibrating element.

6. The assembly as claimed in claim 4, wherein the aperture plate is located within the cavity such that the aperture plate is coupled to a side of the second annular portion which is inward facing to the cavity.

7. The assembly as claimed in claim 1, wherein the vibrating platform is structured such that the aperture plate is positioned within the cavity comprising a conical structure formed by the vibrating platform.

8. The assembly as claimed in claim 1, wherein the vibrating platform is formed from an inverted structure, such that the aperture plate is positioned within a conical structure formed by the vibrating platform.

9. The assembly as claimed in claim 1, wherein the first annular portion of the vibrating platform is fixed to the annular piezoelectric device on a side corresponding to a direction of flow of a fluid during use, and wherein the sidewall and the second annular portion of the vibrating platform project at least into the aperture of the annular piezoelectric device in a direction opposite to the direction of flow, the side corresponding to the direction of flow of the fluid being an upstream side relative to the aperture plate.

10. The assembly as claimed in claim 1, wherein the vibrating platform is structured such that one or more intersections between the first annular portion, second annular portion and sidewall are curved.

11. The assembly as claimed in claim 1, wherein a surface of the first annular portion extending in a radial direction is coupled to a surface of the vibrating element extending in the radial direction, and a surface of the second annular portion is separated from and substantially parallel to the surface of the first annular portion.

12. The assembly as claimed in claim 11, wherein the surface of the first annular portion extending in the radial direction lies in the first plane and the surface of the second annular portion lies in the second plane, the second plane being separated from and substantially in parallel with the first plane, and separated from and substantially in parallel with the third plane corresponding to a plane in which the vibrating element lies.

13. The assembly as claimed in claim 1, wherein a top surface of the first annular portion extending in the radial direction is coupled to a bottom surface of the vibrating element extending in the radial direction, and a top surface and a bottom surface of the second annular portion is separated from and substantially parallel with the bottom surface and a top surface of the vibrating element.

* * * * *